(12) United States Patent
Sailstad

(10) Patent No.: US 10,775,386 B2
(45) Date of Patent: Sep. 15, 2020

(54) METHODS OF DETECTING ANTI-LEPTIN NEUTRALIZING ANTIBODIES

(71) Applicant: Aegerion Pharmaceuticals, Inc., Cambridge, MA (US)

(72) Inventor: Jeffrey Sailstad, Durham, NC (US)

(73) Assignee: Aegerion Pharmaceuticals, Inc., Cambridge, MA (US)

( * ) Notice: Subject to any disclaimer, the term of this patent is extended or adjusted under 35 U.S.C. 154(b) by 186 days.

(21) Appl. No.: 15/702,719

(22) Filed: Sep. 12, 2017

(65) Prior Publication Data

US 2018/0074073 A1 Mar. 15, 2018

Related U.S. Application Data

(60) Provisional application No. 62/393,632, filed on Sep. 12, 2016.

(51) Int. Cl.
*G01N 33/53* (2006.01)
*G01N 33/68* (2006.01)
*G01N 33/74* (2006.01)

(52) U.S. Cl.
CPC ......... *G01N 33/6854* (2013.01); *G01N 33/74* (2013.01); *G01N 2333/575* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,521,283 A | 5/1996 | Dimarchi et al. |
| 5,532,336 A | 7/1996 | Dimarchi et al. |
| 5,552,522 A | 9/1996 | Dimarchi et al. |
| 5,552,523 A | 9/1996 | Basinski et al. |
| 5,552,524 A | 9/1996 | Basinski et al. |
| 5,554,727 A | 9/1996 | Basinski et al. |
| 5,559,208 A | 9/1996 | Basinski et al. |
| 5,580,954 A | 12/1996 | Dimarchi et al. |
| 5,594,101 A | 1/1997 | Becker et al. |
| 5,691,309 A | 11/1997 | Basinski et al. |
| 5,756,461 A | 5/1998 | Stephens |
| 5,851,995 A | 12/1998 | Basinski et al. |
| 5,935,810 A | 8/1999 | Friedman et al. |
| 6,001,968 A | 12/1999 | Friedman et al. |
| 6,309,853 B1 | 10/2001 | Friedman et al. |
| 6,350,730 B1 | 2/2002 | Friedman et al. |
| 6,420,339 B1 | 7/2002 | Gegg et al. |
| 6,429,290 B1 | 8/2002 | Friedman et al. |
| 6,541,033 B1 | 4/2003 | Shah |
| 6,936,439 B2 | 8/2005 | Mann et al. |
| 7,112,659 B2 | 9/2006 | Mann et al. |
| 7,183,254 B2 | 2/2007 | Depaoli et al. |
| 7,208,577 B2 | 4/2007 | Pelleymounter et al. |
| 8,080,254 B2 | 12/2011 | Mann et al. |
| 8,394,765 B2 | 3/2013 | Roth et al. |
| 2005/0209137 A1 | 9/2005 | Gertler et al. |
| 2013/0266963 A1* | 10/2013 | Hauenstein ........ G01N 33/6854 435/7.9 |
| 2016/0083446 A1 | 3/2016 | Erickson |
| 2018/0245076 A1* | 8/2018 | Digenio ............. A61K 31/7125 |

FOREIGN PATENT DOCUMENTS

| | | |
|---|---|---|
| WO | WO 1996/005309 A2 | 2/1996 |
| WO | WO 1996/022308 A2 | 7/1996 |
| WO | WO 1996/023517 A1 | 8/1996 |
| WO | WO 1996/040912 A1 | 12/1996 |
| WO | WO 1997/002004 A2 | 1/1997 |
| WO | WO 1997/006816 A1 | 2/1997 |
| WO | WO 1997/018833 A1 | 5/1997 |
| WO | WO 1997/038014 A1 | 10/1997 |
| WO | WO 1998/006752 A1 | 2/1998 |
| WO | WO 1998/008512 A1 | 3/1998 |
| WO | WO 1998/012224 A1 | 3/1998 |
| WO | WO 1998/028427 A1 | 7/1998 |
| WO | WO 1998/046257 A1 | 10/1998 |
| WO | WO 1998/055139 A1 | 12/1998 |
| WO | WO 2000/009165 A1 | 2/2000 |
| WO | WO 2000/020872 A1 | 4/2000 |
| WO | WO 2000/021574 A2 | 4/2000 |
| WO | WO 2000/047741 A1 | 8/2000 |
| WO | WO 2004/039832 A2 | 5/2004 |
| WO | WO 2005/049655 A1 | 6/2005 |
| WO | WO 2009/064298 A1 | 5/2009 |
| WO | WO 2011/117084 A1 | 9/2011 |
| WO | WO 2012/050925 A2 | 4/2012 |
| WO | WO 2012/050930 A2 | 4/2012 |
| WO | WO 2013/009539 A1 | 1/2013 |
| WO | WO 2018/049424 A1 | 3/2018 |

OTHER PUBLICATIONS

Van Der Vekiens et al., Human and equine cardiovascular endocrinology: beware to compare, Cardiovascular Endocrinology 2013, vol. 2, No. 4, pp. 67-76 (Year: 2013).*

Torzewski et al., Animal Models of C-Reactive Protein, Hindawl Publishing Corporation, Mediators of Inflammation, vol. 2014, Article ID 683598, 2014, pp. 1-7. (Year: 2014).*

Wu et al., Competitive Ligand Binding Assays for the Detection of Neutralizing Antibodies, Practical and Applied Considerations, Jun. 20, 2011, Chapter 10, pp. 175-192. (Year: 2011).*

Beltrand, et al., "Resistance to leptin-replacement therapy in Berardinelli-Seip congenital lipodystrophy: an immunological origin". Eur J Endocrinol. (Jun. 2010); 162(6): 1083-1091.

Chan, et al., "Immunogenicity associated with metreleptin treatment in patients with obesity or lipodystrophy". Clin Endocrinol. (Jul. 2016); 85(1): 137-149. Epub Feb. 2, 2016.

Extended European Search Report in European Application No. 17849795.4 dated Jan. 17, 2020, 8 pages.

(Continued)

*Primary Examiner* — Gary Counts

(74) *Attorney, Agent, or Firm* — Cooley LLP

(57) ABSTRACT

Provided herein are methods for detecting neutralizing antibodies to leptins, including metreleptin, as well as identifying subjects having such neutralizing antibodies.

19 Claims, 8 Drawing Sheets

(56) References Cited

OTHER PUBLICATIONS

Fetissov, et al., "Autoantibodies against appetite-regulating peptide hormones and neuropeptides: Putative modulation by gut microflora". Nutrition (2008); 24(4): 348-359.

International Preliminary Report on Patentability for International Application No. PCT/US2017/051232, dated Mar. 12, 2019, 12 pages.

International Search Report and Written Opinion for International Application No. PCT/US2017/051232, dated Nov. 29, 2017, 15 pages.

Vuolteenaho, et al., "Leptin levels are increased and its negative regulators, SOCS-3 and sOb-R are decreased in obese patients with osteoarthritis: a link between obesity and osteoarthritis". Ann Rheum Dis. (Nov. 2012); 71(11): 1912-1913. Epub Jun. 11, 2012.

Wu, et al., "Quantification of the Soluble Leptin Receptor in Human Blood by Ligand-Mediated Immunofunctional Assay". J Clin Endocrinol Metab. (Jun. 2002); 87(6): 2931-2939.

Zhu, et al., "Streptavidin-biotin-based directional double Nanobody sandwich ELISA for clinical rapid and sensitive detection of influenza H5N1". J Transl Med. (Dec. 20, 2014); 12: 352, 10 pages.

\* cited by examiner

| Sample ID | source | Leptin Signal Leptin | Metreleptin Signal Metreleptin | Results Leptin categorical | % inhibition | Metreleptin categorical | % inhibition | notes |
|---|---|---|---|---|---|---|---|---|
| max signal | NC | 20000.0 | 20000.0 | | | | | could be RFU or Abs depending on final assay format, signal could range from 5,000 up to 500,000 (82,000 ML, 91,000 Leptin) |
| Cutpoint | upper limit of non-specific inhibition | assigned during validation (maybe 10 to 30%, for example make 22%) | assigned during validation (maybe 10 to 30%, for example make 30%) | | | | | the cut point is assigned statistically in validation a point where the lower limit of signal (0.1 or 1% false positive rate is established) across |
| sample 1 | | 19000.0 | 18000.0 | neg | - | neg | - | samples to be tested need to be determined, all samples screened/confirmed at Tandem, which have been tested in the NAb assay |
| sample 2 | | 10000.0 | 18000.0 | pos | 50 | neg | - | |
| sample 3 | | 22000.0 | 5000.0 | neg | - | pos | 75 | |
| sample 4 | | 3000.0 | 5000.0 | pos | 85 | pos | 75 | |
| sample 5 | | 21000.0 | 22000.0 | neg | - | neg | - | |
| sample 6 | | 10000.0 | 10000.0 | pos | 50 | pos | 50 | |
| sample 7 | | 18000.0 | 18000.0 | neg | - | neg | - | |
| sample 8 | | 5000.0 | 20000.0 | pos | 75 | neg | - | |
| sample 9 | | 19000.0 | 18500.0 | neg | - | neg | - | |
| Positive control (low) | | 10000.0 | 10000.0 | pos | 50 | pos | 50 | low and high represent antibody concentration existing neutralizing antibody, limits will be set in validation |
| Positive control (high) | | 1000.0 | 1000.0 | pos | 95 | pos | 95 | |

FIGURE 2

1. Block streptavidin plate with Superblock for 1 hr.
2. Pre-incubate Sample represented by PC antibody + sulfo-tagged Metreleptin for 2 Hr. at RT
3. Wash streptavidin plate and add diluted anti-His antibody in PBS. Incubate 1 hr. at RT.
4. Wash plate and add diluted His-tagged receptor. Incubate 1 hr. at RT.
5. Wash plate and add sulfo-tagged Metreleptin + Ab solution from step 2. Incubate 1 hr. at RT.
6. Wash plate and read on MSD.

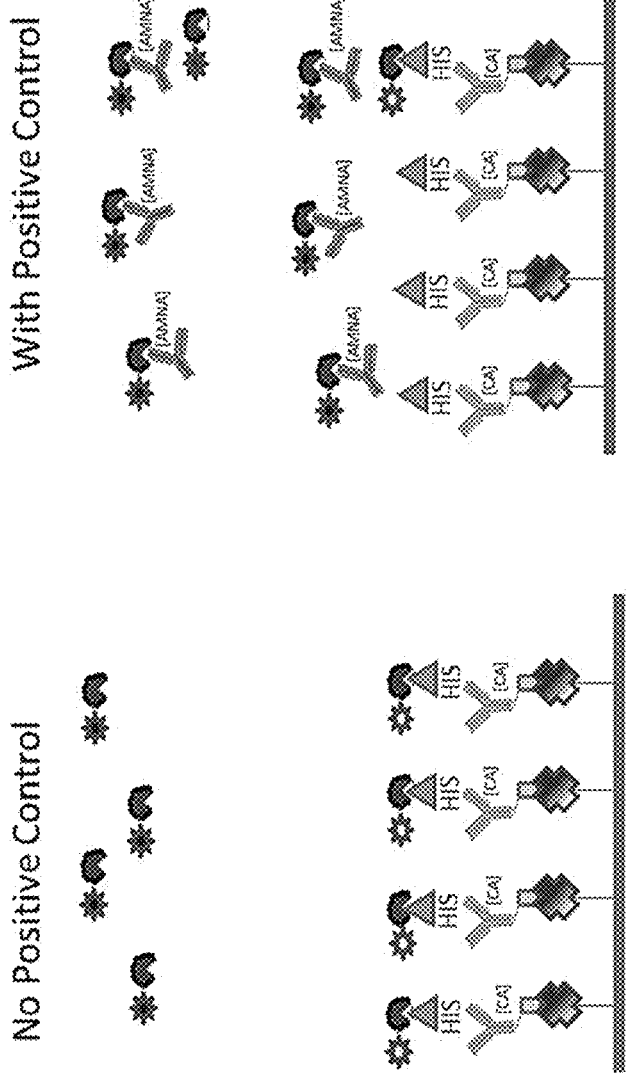

FIGURE 4

1. The procedure described remains the same with the additional pre-treatment step. In what is referred to as a transfer plate the follow occurs.
2. Heat treated samples (PC, NC and samples) are incubated in an acid solution such as 0.8% acetic acid for about an hour.
3. This disassociates antibodies bound to leptin or metreleptin.
4. Labelled leptin or metreleptin is added in a buffer solution (0.125 M Tham buffer), at the moment of addition the labeled material has more opportunity to bind to the antibody. Hence the assay is more drug tolerant.

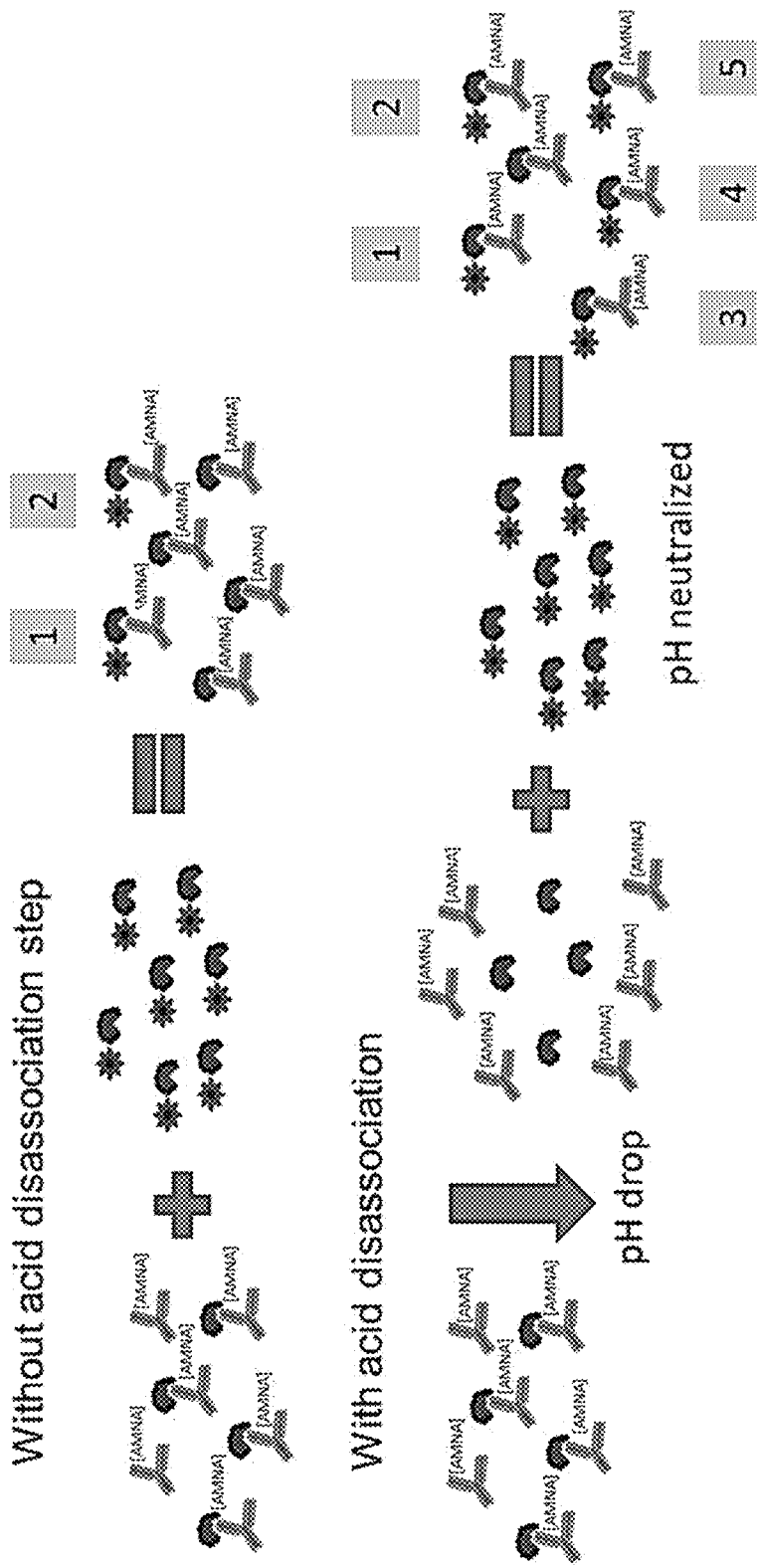

FIGURE 5

| Sample ID | Source | Leptin Max Signal Leptin NC | Leptin cutpoint | Leptin % inhibition | Metreleptin Max Signal Metreleptin NC | Metreleptin cutpoints | Metreleptin % inhibition | Results Leptin categorical | Results Leptin % inhibition | Results Metreleptin categorical | Results Metreleptin % inhibition |
|---|---|---|---|---|---|---|---|---|---|---|---|
| | | 5911 | assigned during validation (10.18 for both disease state and normals) 1% false positive rate | | 2203.5 | assigned during validation (9.66 disease state, 7.89 normals) 1% false positive rate | | | | | |
| sample 1 | Prior Treatment | 5745.0 | 2.81 | | 2138.0 | 2.97 | | neg | - | neg | - |
| sample 2 | | 5548.0 | 6.14 | | 2104.5 | 4.49 | | neg | - | neg | - |
| sample 3 | | 5027.5 | 14.95 | | 1878.5 | 14.75 | | Pos | 15.0 | Pos | 14.8 |
| sample 4 | | 2150.0 | 63.63 | | 724.0 | 67.14 | | Pos | 63.6 | Pos | 67.1 |
| sample 5 | | 599.5 | 89.86 | | 211.5 | 90.40 | | Pos | 89.9 | Pos | 90.4 |
| sample 6 | | 5585.5 | 5.51 | | 2154.0 | 2.25 | | neg | - | neg | - |
| sample 7 | | 481.5 | 91.85 | | 205.5 | 90.67 | | Pos | 91.9 | Pos | 90.7 |
| sample 8 | | 6085.5 | -2.95 | | 2319.0 | -5.24 | | neg | - | neg | - |
| sample 9 | normal non-disease state | 5833.5 | 1.31 | | 2261.0 | -2.61 | | neg | - | neg | - |
| sample 10 | | 5530.5 | 6.44 | | 2206.0 | -0.11 | | neg | - | neg | - |
| sample 11 | | 5856.0 | 0.93 | | 2342.0 | -6.29 | | neg | - | neg | - |
| sample 12 | | 5669.5 | 4.09 | | 2284.5 | -3.68 | | neg | - | neg | - |
| sample 13 | | 5833.0 | 1.32 | | 2304.5 | -4.58 | | neg | - | neg | - |
| sample 14 | | 6382.0 | -7.97 | | 2283.5 | -3.63 | | neg | - | neg | - |
| sample 15 | | 6225.0 | -5.31 | | 2249.5 | -2.09 | | neg | - | neg | - |
| sample 16 | | 5715.5 | 3.31 | | 2225.0 | -0.98 | | neg | - | neg | - |
| sample 17 | | 5995.5 | -1.43 | | 2334.0 | -5.92 | | neg | - | neg | - |
| Positive control (low) | 156 ng/mL 1 | 1804.0 | 30.52 | | 622.0 | 28.23 | | pos | 30.5 | pos | 28.2 |
| Positive control (low) | 156 ng/mL 2 | 1847.2 | 31.25 | | 639.7 | 29.03 | | pos | 31.3 | pos | 29.0 |
| Positive control (high) | 5000 ng/mL 1 | 5770.3 | 97.62 | | 2177.9 | 98.84 | | pos | 97.6 | pos | 98.8 |
| Positive control (high) | 5000 ng/mL 3 | 5755.5 | 97.37 | | 2177.3 | 98.81 | | pos | 97.4 | pos | 98.8 |

FIGURE 6

METHODS OF DETECTING ANTI-LEPTIN NEUTRALIZING ANTIBODIES

CROSS-REFERENCE TO RELATED APPLICATIONS

This application claims the benefit of U.S. Provisional Application Ser. No. 62/393,632, filed on Sep. 12, 2016, which is hereby incorporated by reference in its entirety.

FIELD OF THE DISCLOSURE

The disclosure relates to methods of detecting neutralizing antibodies to leptin, and kits that can be used to perform such methods. Such methods and kits can be used to detect neutralizing antibodies to leptin in a sample, or to identify subjects having neutralizing antibodies to leptin in their blood, serum, or plasma.

BACKGROUND

Metreleptin is a leptin analog indicated as an adjunct to diet as a replacement therapy to treat the complications of leptin deficiency in subjects with congenital or acquired generalized lipodystrophy. Congenital generalized lipodystrophy is a rare condition characterized by an almost total lack of adipose tissue in the body and a very muscular appearance. Adipose tissue is found in many parts of the body, including beneath the skin and surrounding the internal organs. It stores fat for energy and also cushions and insulates the body. A shortage of adipose tissue leads to the storage of fat elsewhere in the body, such as in the liver and muscles, which causes serious health problems. Acquired generalized lipodystrophy is a rare condition that appears during childhood or adolescence, characterized by fat loss affecting large areas of the body, particularly the face, arms, and legs.

In addition, metreleptin is being investigated as a treatment for other indications, including partial lipodystrophy, hypothalamic amenorrhea, nonalcoholic steatohepatitis, and various other hypoleptinemic dysmetabolic disorders.

Metreleptin is generally administered via daily subcutaneous injection. Because of this repeated administration, there is a risk that subjects may develop antibodies to metreleptin. These antibodies may neutralize metreleptin, rendering the treatment ineffective. What is more, they may neutralize endogenous leptin, worsening the disease of subjects already suffering from leptin deficiency. For this reason there is a need in the art of a method of reliably detecting neutralizing antibodies in subjects.

SUMMARY OF THE INVENTION

The present invention relates to the detection of neutralizing antibodies to leptin.

In one aspect, the invention relates to a method of detecting neutralizing antibodies to leptin in a sample, comprising: (a) inactivating leptin present in the sample; (b) adding a known quantity of labeled leptin to the sample; (c) contacting the sample containing labeled leptin of (b) with a substrate capable of binding the labeled leptin; (d) washing the substrate to remove unbound labeled leptin; and (e) measuring the label signal produced by the substrate-bound labeled leptin.

In one aspect, the invention relates to method of identifying a subject having neutralizing antibodies to leptin in blood, serum, or plasma from the subject, comprising (a) inactivating leptin and leptin present in a sample of the subject's blood, serum, or plasma; (b) adding a known quantity of labeled leptin to the sample; (c) contacting the sample containing labeled leptin of (b) with a substrate capable of binding the labeled leptin; (d) washing the substrate to remove unbound labeled leptin; (e) measuring the label signal produced by the bound labeled leptin; (f) measuring a positive control signal, said positive control signal produced by completing steps (a)-(e), and further comprising adding a known quantity of anti-leptin antibody at step (b); and (g) comparing the signal from (e) with the signal from (f), wherein if the level of signal measured in step (e) is equal to or less than the level of signal measured in step (f), then the subject tests positive for anti-leptin neutralizing antibodies.

In another aspect, the present invention relates to a method of identifying subjects having neutralizing antibodies to leptin in blood, serum, or plasma from the subject comprising: (a) inactivating leptin present in a sample of the subject's blood, serum, or plasma; (b) adding a known quantity of labeled leptin to the sample; (c) contacting the sample containing labeled leptin of (b) with a substrate capable of binding the labeled leptin; (d) washing the substrate to remove unbound labeled leptin; (e) measuring the label signal produced by the bound labeled leptin; (f) measuring a negative control signal, said negative control signal produced by completing steps (a)-(e), wherein the sample of blood, serum, or plasma does not contain anti-leptin neutralizing antibodies; and (g) comparing percent difference in the signal from (e) and the signal from (f) with a cutpoint, wherein if the percent difference in the signal from (e) and the signal from (f) is greater than the cutpoint, than the subject tests positive for anti-leptin neutralizing antibodies. In some embodiments, the cutpoint is between about 5% and about 40%, or between about 5% and about 30%, or between about 5% and 15%.

In another aspect, the present invention relates to a method that involves determining in a subject a change in the presence of neutralizing antibodies to leptin in blood, serum, or plasma from the subject over time. In some embodiments, this method may be used in a subject receiving leptin treatment, in which the presence of neutralizing antibodies in the subject's blood, serum, or plasma may be assessed prior to leptin treatment (pre-treatment) and then during or after leptin treatment. The method comprises: (1a) inactivating leptin present in a first sample of the subject's blood, serum, or plasma; (1b) adding a known quantity of labeled leptin to the first sample; (1c) contacting the first sample containing labeled leptin of (1b) with a substrate capable of binding the labeled leptin; (1d) washing the substrate to remove unbound labeled leptin; (1e) measuring the label signal produced by the bound labeled leptin; (2a) inactivating leptin present in a second sample of the subject's blood, serum, or plasma; (2b) adding a known quantity of labeled leptin to the second sample; (2c) contacting the second sample containing labeled leptin of (2b) with a substrate capable of binding the labeled leptin; (2d) washing the substrate to remove unbound labeled leptin; (2e) measuring the label signal produced by the bound labeled leptin; (3) comparing the label signal of (2e) with the label signal of (1e). In some embodiments, the comparison may be determining the percent difference between the label signal of (2e) and the label signal of (1e). In certain embodiments, the percent difference may be compared to a cutpoint. The cutpoint may be between about 55% and about 95%, or between about 60% and about 90%, such as about 65%, or about 85%, or about 80%.

In certain embodiments, the leptin may be labeled with horseradish peroxidase, or ruthenium tris-bipyridine.

In some embodiments, the inactivation of the leptin may be accomplished by heating the sample.

In certain embodiments, the substrate capable of binding the labeled leptin may comprise (i) a coated matrix, and (ii) a tagged leptin receptor bound to the matrix of (i). The coated matrix may be a streptavidin-coated matrix. The leptin receptor may be tagged with biotin.

In some embodiments, the substrate capable of binding the labeled leptin may comprise (i) a coated matrix, (ii) an antibody bound to the matrix of (i), and (iii) a tagged leptin receptor bound to the antibody of (ii). The coated matrix may be a streptavidin-coated matrix. The leptin receptor may be tagged with a tag suitable for affinity purification; for example, the leptin receptor may be tagged with a hexa-histidine tag. The antibody may have a suitable affinity for the leptin receptor tag; for instance, the antibody may be an anti-hexa histidine antibody. Further, the antibody may be labeled with a tag suitable to bind to the coated matrix, such as biotin.

The methods of the present invention may further comprise a step of decreasing the pH of the inactivated sample (a) by the addition of an acidic solution, and wherein labeled leptin added in (b) further comprise a basic solution sufficient to neutralize the pH of the sample after addition. The acidic solution may be an acetic acid solution, such as a 0.8% acetic acid. The basic solution may be a buffer, such as a 0.125 M Tham buffer.

In some embodiments, the labeled leptin added in step (b) may be a recombinant human leptin. In certain embodiments, the labeled leptin added in step (b) may be metreleptin.

In some embodiments, the detectable signal is generated in step (e) when the concentration of labeled leptin, such as metreleptin, in the sample at step (b) is between about 90 ng/mL and about 120 ng/mL, or between about 100 ng/mL and about 110 ng/mL, such as about 101 ng/mL, or about 109 ng/mL.

In one aspect, the invention relates to method of determining responsiveness of a subject having a leptin-related disorder to treatment with leptin, comprising determining the amount of anti-leptin neutralizing antibodies in the subject, wherein the amounts of the antibodies is predictive of non-responsiveness of the subject to leptin therapy. The methods may comprise the step listed above. The leptin-related disorder may be congenital generalized lipodystrophy, acquired generalized lipodystrophy, partial lipodystrophy, hypothalamic amenorrhea, nonalcoholic steatohepatits, and hypoleptinemic dysmetabolic disorder.

In another aspect, the invention relates to a kit that can be used to detecting neutralizing antibodies to leptin in a sample. The kit may comprise (a) labeled leptin, and (b) a substrate capable of binding the labeled leptin.

In certain embodiments, the leptin in the kit may be labeled with horseradish peroxidase, or ruthenium tris-bipyridine.

In some embodiments, the substrate in the kit may comprise (i) a coated matrix, and (ii) a tagged leptin receptor bound to the matrix of (i). The coated matrix may be a streptavidin-coated matrix. The leptin receptor may be tagged with biotin. The coated matrix and the tagged leptin receptor may be together as one component in the kit, or may be separate components.

In some embodiments, the substrate in the kit may comprise (i) a coated matrix, (ii) an antibody bound to the matrix of (i), and (iii) a tagged leptin receptor bound to the antibody of (ii). The coated matrix may be a streptavidin-coated matrix. The leptin receptor may be tagged with a tag suitable for affinity purification; for example, the leptin receptor may be tagged with a hexa-histidine tag. The antibody may have a suitable affinity for the leptin receptor tag; for instance, the antibody may be an anti-hexa histidine antibody. Further, the antibody may be labeled with a tag suitable to bind to the coated matrix, such as biotin. The coated matrix, the antibody, and the tagged leptin receptor may be together as one component in the kit, or as separate components.

In certain embodiments, the kit may further comprise a positive control and/or a negative control.

In some embodiments, the kit may further comprise an acidifying reagent; for example, an acetic acid.

In certain embodiments, the kit may further comprise a basic solution; for example, a buffer such as a Tham buffer.

BRIEF DESCRIPTION OF THE FIGURES

The present disclosure will be further explained with reference to the attached drawing figures. The drawing figures shown are not necessarily to scale, with emphasis instead generally being placed upon illustrating the principles of the present disclosure, and some features may be exaggerated to show details of particular components. In addition, any measurements, specifications and the like shown in the drawing figures, or described below, are intended to be illustrative, and not restrictive. Therefore, specific structural and functional details disclosed herein are not to be interpreted as limiting, but merely as a representative basis for teaching one skilled in the art to employ the methods and kits described herein.

FIG. 1A describes the various components used in the assay, and FIG. 1B illustrates the application of the assay.

FIG. 2 presents an exemplary data sheet for presenting the results of a receptor binding assay according to embodiments of the invention.

FIG. 3A describes the various components used in the assay, and FIG. 3B illustrates the application of the assay.

FIG. 4 depicts an exemplary receptor binding assay for metreleptin that involves positive and negative controls, according to embodiments of the invention.

FIG. 5 depicts an acid disassociation step for use in an exemplary receptor binding assay for metreleptin, according to embodiments of the invention.

FIG. 6 is a table which presents signal, % inhibition, as well as categorical data gathered from the analysis of samples from 17 subjects, some of which were healthy, and some of which were diseased and had been previously treated with leptin.

DETAILED DESCRIPTION

Figure 1A:
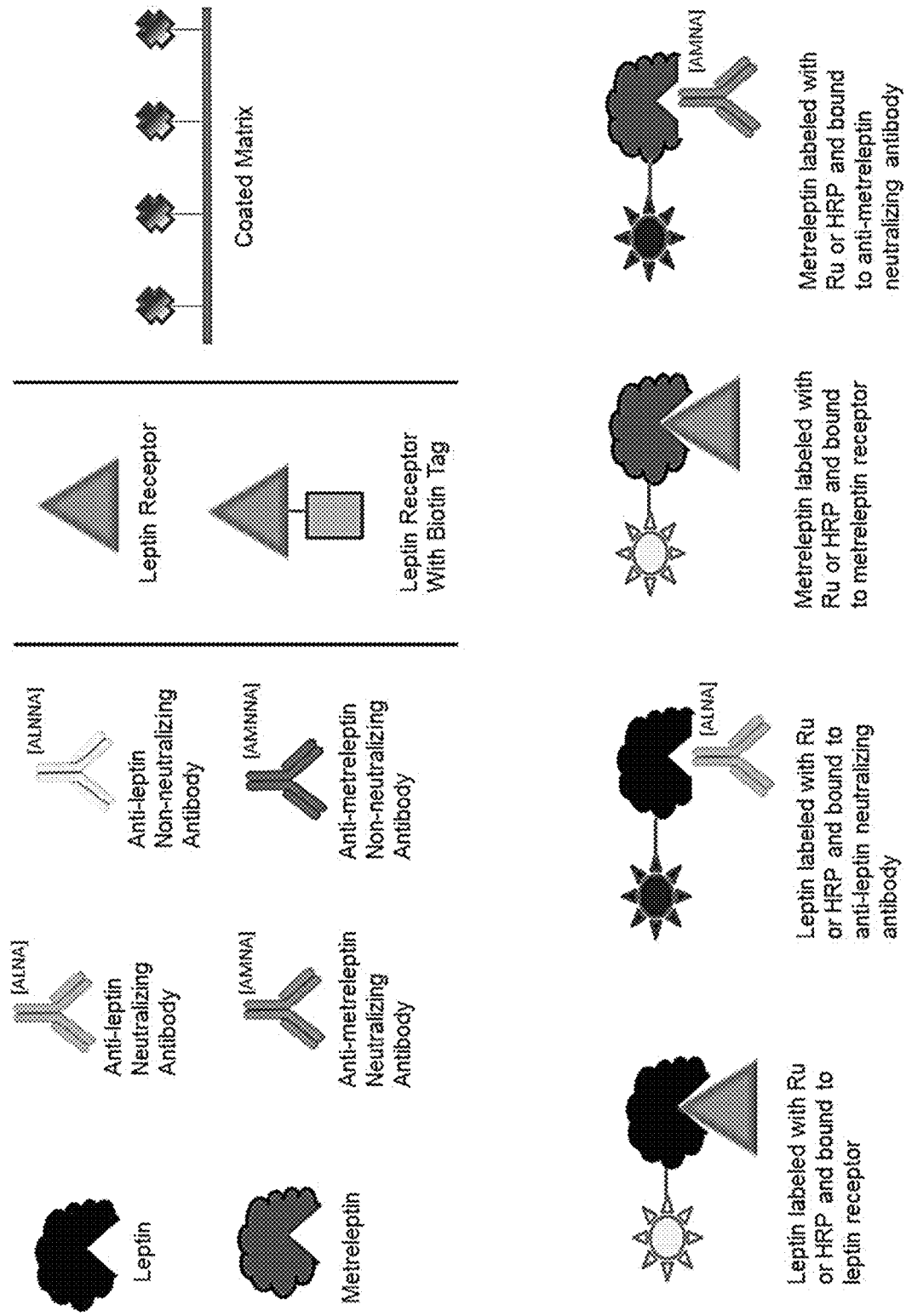
FIG. 1A-1B depicts an exemplary receptor binding assay for leptin and metreleptin that involves a substrate capable of binding the labeled leptin, comprising (i) a coated matrix, and (ii) a tagged leptin receptor bound to the matrix of (i), according to embodiments of the invention.

Methods for Detecting Neutralizing Antibodies to Leptin

Described herein are methods for detecting neutralizing antibodies to leptin in a sample. Exemplary methods comprise the steps of (a) inactivating leptin present in the sample; (b) adding a known quantity of labeled leptin to the sample; (c) contacting the sample containing labeled leptin of (b) with a substrate capable of binding the labeled leptin; (d) washing the substrate to remove unbound labeled leptin; and (e) measuring the label signal produced by the substrate-bound labeled leptin.

The term "method" and "assay" are used interchangeably herein.

It is contemplated that the methods disclosed herein may be used to detect neutralizing antibodies to leptin of any species, including naturally occurring human, mouse, rat, and other heterologous species leptins, as well as recombinantly produced mature leptin. For example, leptin is the polypeptide product, for instance, of the ob gene as described in International Publication No. WO 96/05309, and U.S. Pat. No. 6,309,853, each of which is incorporated herein by reference in its entirety. The methods of the invention may also be used to detect neutralizing antibodies to leptin biologically active fragments, agonist, agonist analogs, variants, fusion proteins, chimeric leptin, and other derivatives thereof, such as those compounds disclosed in U.S. Pat. Nos. 5,521,283, 5,532,336, 5,552,522, 5,552,523, 5,552,524, 5,554,727, 5,559,208, 5,580,954, 5,594,101, 5,691,309, 5,756,461, 5,851,995, 5,935,810, 6,001,968, 6,309,853, 6,309,853, 6,350,730, 6,420,339, 6,429,290, 6,541,033, 6,936,439, 7,112,659, 7,183,254, 7,208,577, 8,080,254, 8,394,765, U.S. Publication No. 2016/0083446, PCT Publication No. WO 00/09165, PCT Publication No. WO 00/20872, PCT Publication No. WO 00/21574, PCT Publication No. WO 00/47741, PCT Publication No. WO 04/39832, PCT Publication No. WO 09/64298, PCT Publication No. WO 96/05309, PCT Publication No. WO 96/22308, PCT Publication No. WO 96/23517, PCT Publication No. WO 96/40912, PCT Publication No. WO 97/02004, PCT Publication No. WO 97/06816, PCT Publication No. WO 97/18833, PCT Publication No. WO 97/38014, PCT Publication No. WO 98/08512, PCT Publication No. WO 98/12224, PCT Publication No. WO 98/28427, PCT Publication No. WO 98/46257, PCT Publication No. WO 98/55139, PCT Publication No. WO 2012/050925, PCT Publication No. WO 2012/050930, and PCT Publication No. WO 2013/009539; each of which is hereby incorporated by reference in its entirety and for all purposes. In certain embodiments, the methods of the invention may be used to detect neutralizing antibodies to metreleptin.

Contemplated methods of inactivating leptin include heat inactivation, as well as treatment with chemical inhibitors of leptin, including chemical poisons of leptin, provided that the inhibitors or poisons can be inactivated prior to the addition of labeled leptin.

It is contemplated that the labeled leptin can be any form of leptin, leptin analog, leptin chimera or fusion protein, or derivative thereof, including those compounds listed above. It is contemplated that the labeled leptin may be labeled with any label capable of producing a conveniently quantified signal. Labels may be fluorescent tags, including time-resolved fluorescent tags. Examples include horseradish peroxidase, alkaline phosphatase, and ruthenium tris-bipyridine, among other tags known in the art. A person of skill in the art will understand that the method of detecting the label signal produced by the substrate-bound labeled leptin will depend on the nature of the label.

It is contemplated that the substrate used to contact the sample-containing labeled leptin may comprise (i) a coated matrix; and (ii) a tagged leptin receptor bound to the matrix. In some embodiments, the coated matrix is a streptavidin-coated matrix. In certain embodiments, the leptin receptor is tagged with biotin. For example, the leptin receptor may be bound to the matrix via the biotin. It is understood that the coated matrix may be bound by more than one tagged leptin receptor. In certain embodiments, an analog of the leptin receptor may be bound to the matrix.

Alternatively, it is contemplated that the substrate may comprise: (i) a coated matrix; (ii) an antibody bound to the matrix; and (iii) a tagged leptin receptor bound to the antibody. In some embodiments, the coated matrix is a streptavidin-coated matrix. In certain embodiments, the leptin receptor may be tagged with any tag suitable for affinity purification. For instance, the tag may be a hexa-histidine tag. In some embodiments, the antibody, which may be referred to as "leptin-receptor-capture antibody," is any antibody with suitable affinity for the leptin receptor tag. For example, the leptin-receptor-capture antibody may be an anti-hexa histidine antibody, if the leptin receptor has a hexa-histidine tag. The leptin-receptor-capture antibody may also be labeled with a tag suitable to bind it to the matrix, for example, biotin. In certain embodiments, an analog of the leptin receptor may be bound to the matrix.

The matrix as used herein may be a solid support onto which a tagged leptin receptor or an antibody is bound. The matrix may be appropriate to measure the signal produced by the labeled leptin. Examples of a matrix include, but are not limited to, the wells of a plate, such as a microtiter plate, and beads. In certain embodiments, the matrix may be a Meso Scale Discovery (MSD) multiwell plate.

In certain embodiments, the sample used in the present methods for detecting neutralizing antibodies to leptin may be selected from blood, serum, or plasma of a subject. The subject may be a mammal, such as a human.

In an aspect of the invention, the methods contemplated herein may be used to identify subjects having neutralizing antibodies in, for example, their blood, serum, or plasma. It is contemplated that individuals having neutralizing antibodies for any leptin or leptin analog may be identified. Individuals who are positive for neutralizing antibodies may be identified by comparing the signal produced by labeled leptin with positive and/or negative control data. When the control is a positive control, it is contemplated that where the signal is less than or equal to the positive control signal, the sample will be scored as positive for neutralizing antibodies. Where the control is a negative control, the percent difference between the sample signal and the control signal will be calculated, and the percent difference will be compared against a cutpoint, and if it is greater than the cutpoint, the subject is diagnosed with having neutralizing antibodies to the tested leptin.

Figure 1B:
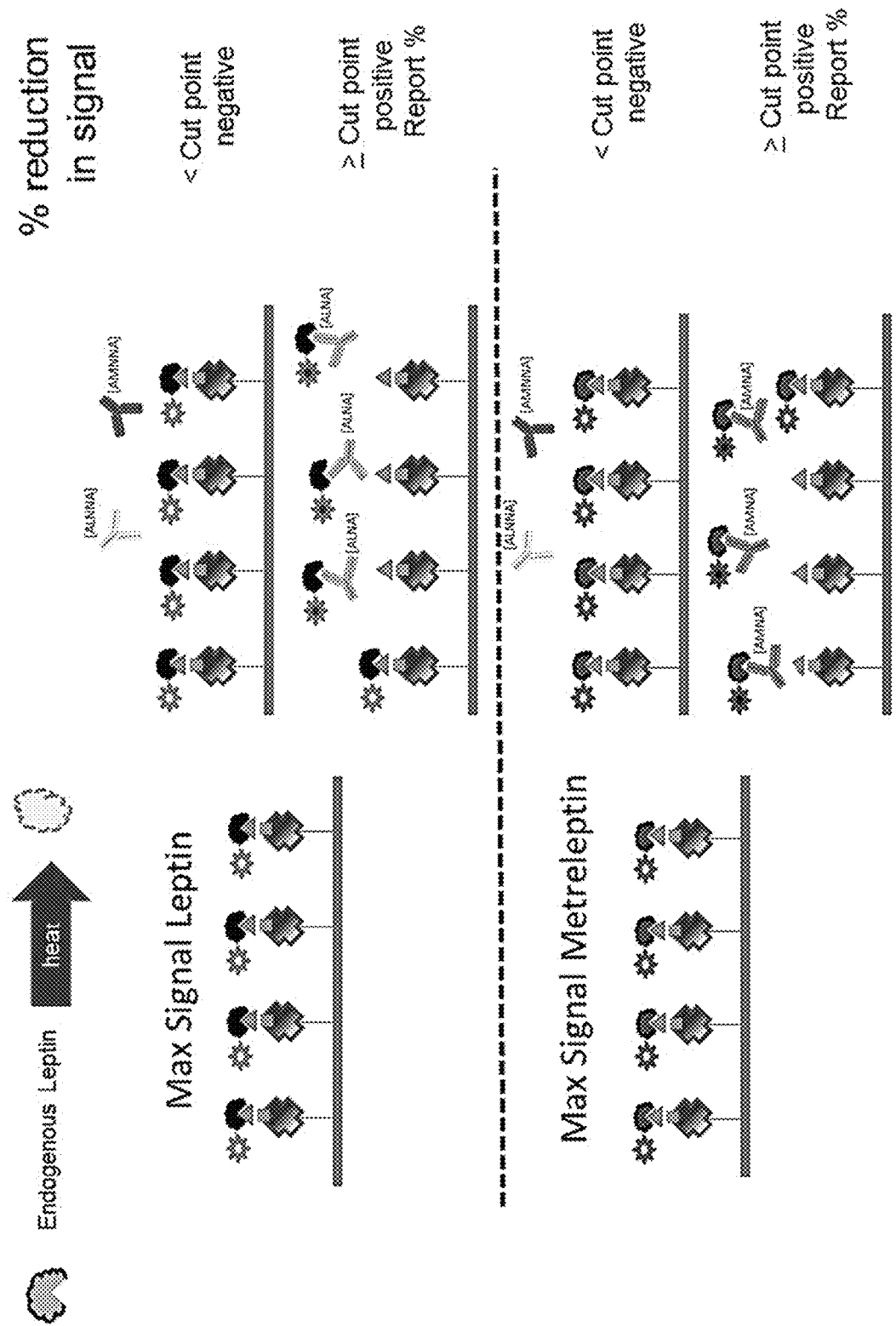
Figure 3A:
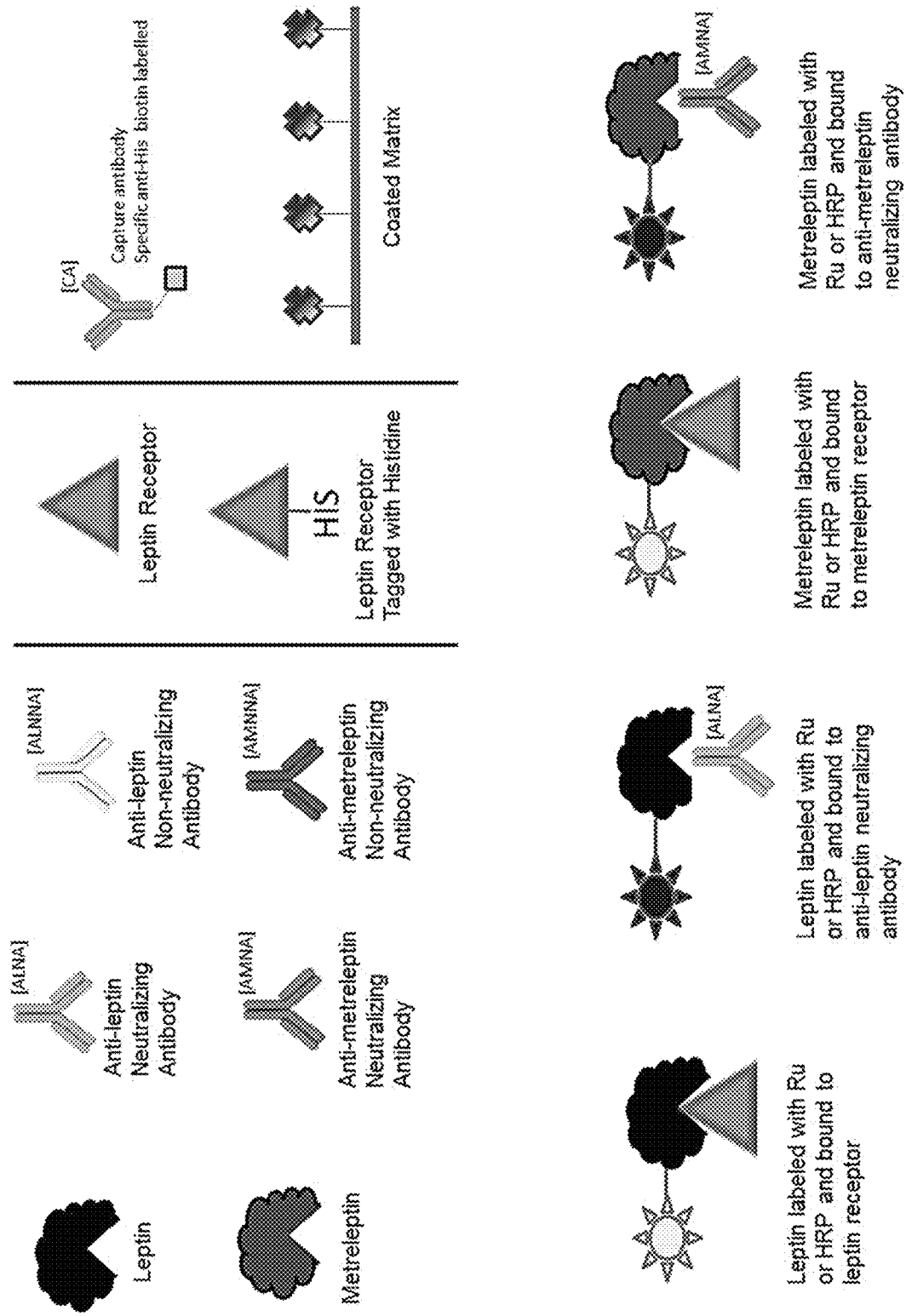
FIG. 3A-3B depicts an exemplary receptor binding assay for leptin and metreleptin that involves a substrate capable of binding the labeled leptin, comprising (i) a coated matrix, (ii) an antibody bound to the matrix of (i), and (iii) a tagged leptin receptor bound to the antibody of (ii), according to embodiments of the invention.
Figure 3B:
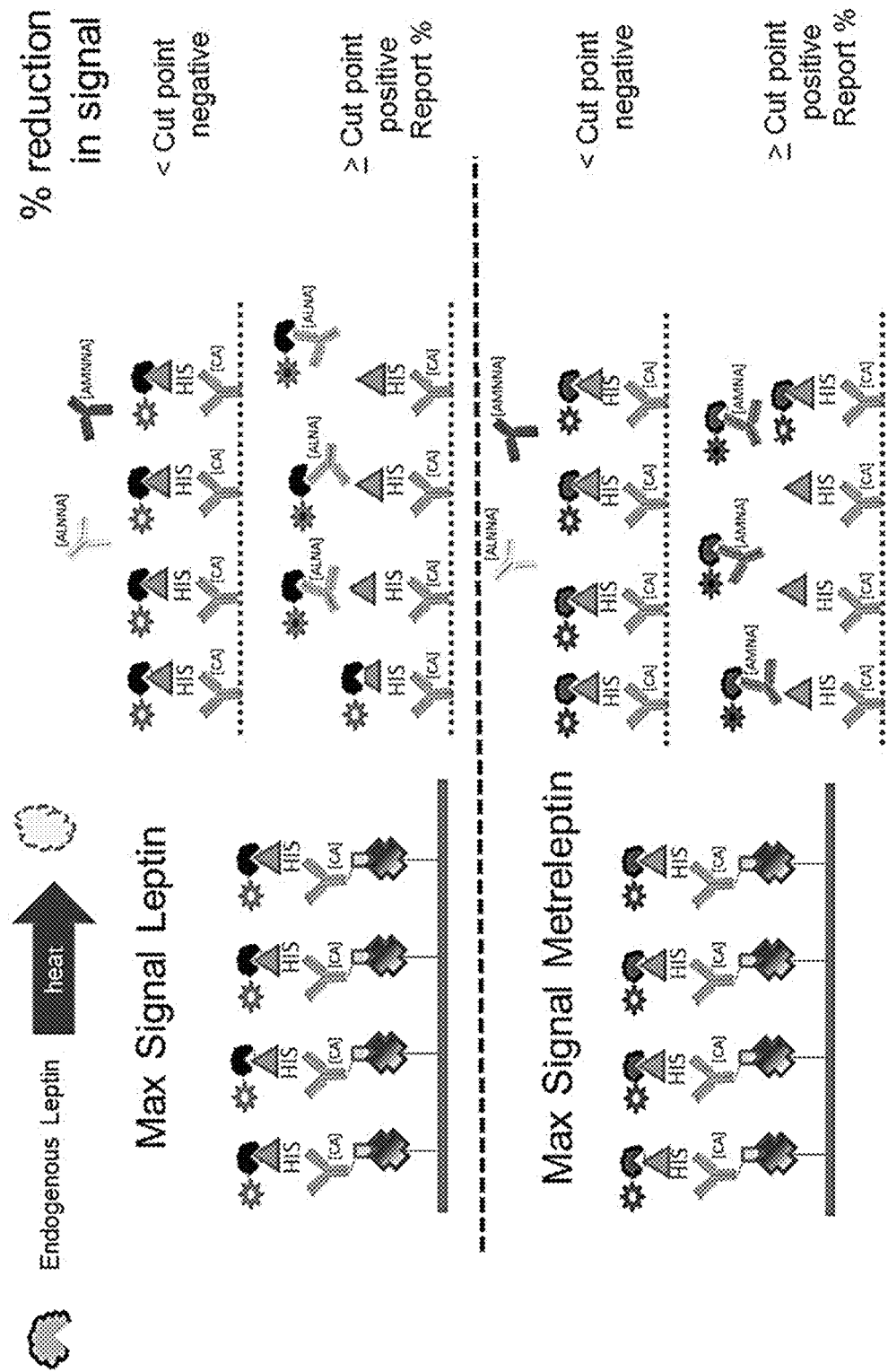

Embodiments of the method involving a negative control are illustrated in FIGS. 1A-1B and 3A-3B. These figures demonstrate how binding can occur between labeled leptin/metreleptin and leptin receptors, and/or between anti-leptin/anti-metreleptin neutralizing antibodies and leptin receptors, to result in a percent difference in signal that is less than the cutpoint, or equal to or greater than the cutpoint.

The cutpoint may be between about 5% and about 40%, or between about 10% and about 30%, or about 20%. For example, the cutpoint may be about 5%, or about 6%, or 7%, or about 8%, or about 9%, or about 10%, or about 11%, or about 12%, or about 13%, or about 14%, or about 15%, or about 16%, or about 17%, or about 18%, or about 19%, or about 20%, or about 21%, or about 22%, or about 23%, or about 24%, or about 25%, or about 26%, or about 27%, or about 28%, or about 29%, or about 30%, or about 31%, or about 32%, or about 33%, or about 34%, or about 35%, or about 36%, or about 37%, or about 38%, or about 39%, or about 40%.

In certain embodiments, the cutpoint may differ if the subject has a normal leptin level, or if the subject has a leptin deficiency. In certain embodiments, a subject has a leptin deficiency if he/she has a serum concentration that is about 16 ng/mL or below for a female and about 7 ng/mL or below for a male; a serum concentration that is about 8 ng/mL or below for a female and about 5 ng/mL or below for a male; or about 5 ng/mL or below for a female, and about 3 ng/mL or below for a male. Or, a subject has a leptin deficiency if he/she has a serum concentration within the 15th percentile, or the 10th percentile, or the 8th percentile, or the second percentile, or the first percentile per NHANES III. Alternatively, a subject has a leptin deficiency if he/she has a serum concentration that is within a specified percentile adjusted for BMI, gender, and/or other factors, such a serum concentration within the 10th percentile, or the 5th percentile, or the 3rd percentile, or the 2nd percentile, per NHANES III, adjusted for BMI.

In certain embodiments where the subject does not have a leptin deficiency, the cutpoint will be between about 5% and about 40%, or between about 5% and about 30%, or in some embodiments between about 5% and about 15%, such as about 10.2% if neutralizing antibodies to leptin is being detected (e.g., if the subject was being treated with leptin), or about 7.89% if neutralizing antibodies to metreleptin is being detected (e.g., if the subject was being treated with metreleptin). In certain embodiments where the subject has a leptin deficiency, the cutpoint will be between about 5% and about 40%, or between about 5% and about 30%, or in some embodiments between about 5% and about 15%, such as about 10.2% if neutralizing antibodies to leptin is being detected (e.g., if the subject was being treated with leptin), or about 9.66% if neutralizing antibodies to metreleptin is being detected (e.g., if the subject was being treated with metreleptin).

FIG. 2 presents an exemplary data sheet for use with the methods of the invention.

In an aspect, the methods contemplated herein may be used to determine in a subject a change in the presence of neutralizing antibodies to leptin in blood, serum, or plasma from the subject over time. For, example, the methods may used in a subject undergoing leptin treatment to assess a change in the presence of neutralizing antibodies in the subject's blood, serum, or plasma prior to leptin treatment and then during or after leptin treatment. Examples of treatments with leptin are known in the art. The method may comprise: (1a) inactivating leptin present in a first sample of the subject's blood, serum, or plasma; (1b) adding a known quantity of labeled leptin to the first sample; (1c) contacting the first sample containing labeled leptin of (1b) with a substrate capable of binding the labeled leptin; (1d) washing the substrate to remove unbound labeled leptin; (1e) measuring the label signal produced by the bound labeled leptin; (2a) inactivating leptin present in a second sample of the subject's blood, serum, or plasma; (2b) adding a known quantity of labeled leptin to the second sample; (2c) contacting the second sample containing labeled leptin of (2b) with a substrate capable of binding the labeled leptin; (2d) washing the substrate to remove unbound labeled leptin; (2e) measuring the label signal produced by the bound labeled leptin; (3) comparing the label signal of (2e) with the label signal of (1e). In some embodiments, the comparison may be determining the percent difference between the label signal of (2e) and the label signal of (1e). In certain embodiments, the percent difference may be compared to a cutpoint. The cutpoint may be between about 55% and about 95%, or between about 60% and about 90%. Examples include about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%. In certain embodiments, the cutpoint may be used to determine whether the subject should continue the treatment, or whether the subject will be responsive to the treatment. For example, if the percent difference is equal to or less than the cutpoint, it may be determined that the subject should discontinue the treatment, or that the subject will not be responsive to the treatment.

Contemplated methods may further comprise a disassociation step, in order to disassociate any neutralizing antibodies in the sample from any leptin that may be present in the sample. Said disassociation step may be accomplished by decreasing the pH of the sample after leptin neutralization. Suitable reagents for acidifying the sample will be readily apparent to one of skill in the art, for example, acetic acid may be used, such as a solution of about 0.5% to about 1% acetic acid, or about 0.8% acetic acid. Other suitable reagents that can be used to acidify the sample would be known to one of ordinary skill in the art. Following acidification of the sample, which disassociates any neutralizing antibodies from leptins that may be present in the sample, labeled leptin may be added together with a basic solution sufficient to neutralize the pH of the sample. It is contemplated that the solution containing the labeled leptin may be a buffer, such that when it is added to the sample, the pH of the sample is raised to approximately 7, such as 7.4, allowing any neutralizing antibodies present in the sample to bind to the labeled leptin. Appropriate buffers include Tham buffer of about 0.1 M to about 0.15 M, or about 0.12 M to about 0.14 M, or about 0.124 M or 0.125 M. Other suitable buffers that can return the pH of the sample to around neutrality would be known to one of ordinary skill in the art.

The signals produced by the labels may be measured by methods known in the art. For example, suitable devices that can measure the signals would be known to one of ordinary skill in the art.

It is contemplated that a determination as to whether or not a subject has neutralizing antibodies to leptin may be used to predict whether the subject will be responsive to treatment with leptin, for example, a subject with high levels of neutralizing antibodies would be expected to be non-responsive to leptin treatment.

Kits

Another aspect of the present invention is a kit comprising the components for performing the methods of the invention. Such a kit may comprise labeled leptin and a substrate capable of binding the labeled leptin as described above for use in the methods of the invention. For example, in some embodiments, the leptin may be labeled with horseradish peroxidase, alkaline phosphatase, or ruthenium tris-bipyridine. In certain embodiments, the leptin is metreleptin.

In certain embodiments, the substrate may comprise a coated matrix as described above, such as a streptavidin-coated matrix, and a tagged leptin receptor. The leptin receptor may be tagged with biotin. In some embodiments, the coated matrix and the tagged leptin receptor may be stored in the kit separately. In other embodiments, the tagged leptin receptor may be bound to the coated matrix.

In some embodiments, the substrate may comprise a coated matrix, such as a streptavidin-coated matrix; an antibody; and a tagged leptin receptor. The leptin receptor may be tagged with any tag suitable for affinity purification, such as a hexa-histidine tag. In some embodiments, the antibody, i.e., leptin-receptor-capture antibody, is any antibody with suitable affinity for the leptin receptor tag. For example, the leptin-receptor-capture antibody may be an anti-hexa histidine antibody, if the leptin receptor has a hexa-histidine tag. The leptin-receptor-capture antibody may also be labeled with a tag suitable to bind it to the matrix, such as biotin. In some embodiments, the antibody may be bound to the matrix, and/or the tagged leptin receptor may be bound to the antibody. In other embodiments, the coated matrix, the antibody, and the tagged leptin receptor are in the kit separately.

In certain embodiments, the kit further comprises a positive control, such as an anti-leptin or anti-metreleptin antibody.

In certain embodiment, the kit further comprises a negative control.

In some embodiments, the kit further comprises one or more acidifying reagents. For example, the acidifying reagent may be an acetic acid, such as a solution of about 0.5% to about 1% acetic acid, or about 8% acetic acid.

In some embodiments, the kit further comprises a basic solution, such as a buffer. Appropriate buffers include a Tham buffer of about 0.1 M to about 0.15 M, or about 0.12 M to about 0.14 M, or about 0.124 M or 0.125 M.

In some embodiments, the kit further comprises instructions for operating the components in the kit.

EXAMPLES

The examples which follow are intended in no way to limit the scope of this invention but are provided to illustrate aspects of the disclosed methods. Many other embodiments of this invention will be apparent to one skilled in the art.

Example 1

Subject samples may be tested as follows in order to determine the level of neutralizing antibodies they contain (see also FIG. 4):
1. Streptavidin coated plates are blocked using Superblock for 1 hour.
2. Subject samples are heat inactivated.
3. Ruthenium (Ru) sulfo-tagged leptin or metreleptin is added to each sample. Positive control samples are prepared by adding Ru sulfo-tagged leptin or metreleptin and the anti-leptin positive control antibody muLEP13-11.03. Samples are incubated at room temperature for 2 hours.
4. Streptavidin plates are washed with phosphate-buffered saline (PBS). Biotin labeled anti-hexa histidine antibody diluted in PBS is added to plates and incubated at room temperature for 1 hour.
5. Plates are washed with PBS, and diluted hepta-histidine tagged leptin receptor protein is added to the plates, and plates are incubated at room temperature for one hour.
6. Plates are washed with PBS, and test and control samples (from step 2 above) are added to the plates, and plates are incubated at room temperature for 1 hour.
7. Plates are washed with PBS and read on MSD ESL reader.

Maximum signal for negative control wells containing leptin and metreleptin, but no neutralizing antibody, is measured. Percent inhibition is calculated by subtracting the difference between the maximum signal and the measured signal for each sample, and dividing that number by the maximum signal. Percent inhibition is then compared to a cutpoint, as described in Example 3.

Example 2

An optional acid disassociation step may be performed by modifying the procedure described in Example 1 as follows (see also FIG. 5):
1. After heat inactivation, samples are incubated in 0.8% acetic acid solution at room temperature for one hour to disassociate any bound antibodies in the sample.
2. Sulfo-tagged leptin or metreleptin are diluted in 0.124 M Tham buffer solution, which neutralizes the acetic sample upon addition, allowing antibody binding It was determined that the sensitivity of the receptor binding assay described above was 109 ng/mL for antibodies to metreleptin and 101 ng/mL for antibodies to leptin. The limit of detection for a comparable cell based neutralizing antibody assay was 251 ng/mL.

Example 3

Cutpoints were calculated based on percent inhibition of leptin and metreleptin signal in diseased subjects that had had previous metreleptin treatment, and normal, non-diseased treatment. The cutpoint for leptin binding inhibition in normal and previously treated diseased subjects was 10.18% inhibition. The cutpoint for metreleptin binding inhibition in subjects that had had previously treated diseased subjects was 9.66% inhibition, and in normal subjects it was 7.89% inhibition. All cutpoints were set to give a 1% false positive rate. Cutpoint data is presented in FIG. 6.

TABLE 1

A summary of the cutpoints for Leptin and Metreleptin for both normal and diseased subjects.

| Leptin | | Metreleptin | |
| --- | --- | --- | --- |
| Max Signal Leptin NC | cutpoint | Max Signal Metreleptin NC | cutpoints |
| 5911 | assigned during validation (10.2 for both disease state and normal) 1% false positive rate | 2203.5 | assigned during validation (9.66 disease state, 7.89 normal) 1% false positive rate |

Example 4

Samples from 17 patients were tested for leptin and metreleptin signal inhibition according to the methods described above. Data is presented in FIG. 6, and tables 2-4.

Two control monoclonal anti-leptin neutralizing antibodies were used at concentrations of either 156 ng/ml (Positive control (low)) or 5000 ng/mL (Positive control (high)). Control data are presented in FIG. 6 and Table 3. Inhibition by both antibodies was remarkably consistent, showing the robustness of the assay.

Samples with inhibition greater than the cutpoint were assigned to the positive category, where as those with inhibition below the cutpoint were assigned to the negative category. See FIG. 6 and Table 4.

TABLE 2

Signal data and percent inhibition of leptin and metreleptin binding from samples from 17 patients.

| Sample ID | Source | Leptin Max Signal Leptin NC 5911 signal | Leptin cutpoint assigned during validation (10.18 for both disease state and normals) 1% false positive rate % inhibition | Metreleptin Max Signal Metreleptin NC 2203.5 signal | Metreleptin cutpoints assigned during validation (9.66 disease state, 7.89 normals) 1% false positive rate % inhibition |
|---|---|---|---|---|---|
| sample 1 | Prior | 5745.0 | 2.81 | 2138.0 | 2.97 |
| sample 2 | Treatment | 5548.0 | 6.14 | 2104.5 | 4.49 |
| sample 3 | | 5027.5 | 14.95 | 1878.5 | 14.75 |
| sample 4 | | 2150.0 | 63.63 | 724.0 | 67.14 |
| sample 5 | | 599.5 | 89.86 | 211.5 | 90.40 |
| sample 6 | | 5585.5 | 5.51 | 2154.0 | 2.25 |
| sample 7 | | 481.5 | 91.85 | 205.5 | 90.67 |
| sample 8 | | 6085.5 | −2.95 | 2319.0 | −5.24 |
| sample 9 | normal | 5833.5 | 1.31 | 2261.0 | −2.61 |
| sample 10 | non- | 5530.5 | 6.44 | 2206.0 | −0.11 |
| sample 11 | disease | 5856.0 | 0.93 | 2342.0 | −6.29 |
| sample 12 | state | 5669.5 | 4.09 | 2284.5 | −3.68 |
| sample 13 | | 5833.0 | 1.32 | 2304.5 | −4.58 |
| sample 14 | | 6382.0 | −7.97 | 2283.5 | −3.63 |
| sample 15 | | 6225.0 | −5.31 | 2249.5 | −2.09 |
| sample 16 | | 5715.5 | 3.31 | 2225.0 | −0.98 |
| sample 17 | | 5995.5 | −1.43 | 2334.0 | −5.92 |

TABLE 3

Signal data and percent inhibition of leptin and metreleptin binding by high and low doses of positive control monoclonal anti-leptin neutralizing antibodies.

| Sample ID | Source = monoclonal | | Leptin Max Signal Leptin NC 5911 signal | Leptin cutpoint assigned during validation (10.18 for both disease state and normals) 1% false positive rate % inhibition | Metreleptin Max Signal Metre- leptin NC 2203.5 signal | Metreleptin cutpoints assigned during validation (9.66 disease state, 7.89 normals) 1% false positive rate % inhibition |
|---|---|---|---|---|---|---|
| Positive control (low) | 156 ng/mL | 1 | 1804.0 | 30.52 | 622.0 | 28.23 |
| | | 2 | 1847.2 | 31.25 | 639.7 | 29.03 |
| Positive control (high) | 5000 ng/mL | 1 | 5770.3 | 97.62 | 2177.9 | 98.84 |
| | | 2 | 5755.5 | 97.37 | 2177.3 | 98.81 |

TABLE 4

Signal data, and percent inhibition of leptin and metreleptin binding, and diagnosed category (positive or negative for neutralizing anti-leptin antibodies) for samples from 17 patients.

| Sample ID | Source | Leptin Max Signal Leptin NC 5911 signal | Metreleptin Max Signal Metreleptin NC 2203.5 signal | Results Leptin category | Results Leptin % inhibition | Results Metreleptin category | Results Metreleptin % inhibition |
|---|---|---|---|---|---|---|---|
| 1 | Prior | 5745.0 | 2138.0 | neg | — | neg | — |
| 2 | Treatment | 5548.0 | 2104.5 | neg | — | neg | — |
| 3 | | 5027.5 | 1878.5 | Pos | 15.0 | Pos | 14.8 |
| 4 | | 2150.0 | 724.0 | Pos | 63.6 | Pos | 67.1 |
| 5 | | 599.5 | 211.5 | Pos | 89.9 | Pos | 90.4 |
| 6 | | 5585.5 | 2154.0 | neg | — | neg | — |
| 7 | | 481.5 | 205.5 | Pos | 91.9 | Pos | 90.7 |
| 8 | | 6085.5 | 2319.0 | neg | — | neg | — |
| 9 | normal non- | 5833.5 | 2261.0 | neg | — | neg | — |
| 10 | disease state | 5530.5 | 2206.0 | neg | — | neg | — |
| 11 | | 5856.0 | 2342.0 | neg | — | neg | — |
| 12 | | 5669.5 | 2284.5 | neg | — | neg | — |
| 13 | | 5833.0 | 2304.5 | neg | — | neg | — |
| 14 | | 6382.0 | 2283.5 | neg | — | neg | — |
| 15 | | 6225.0 | 2249.5 | neg | — | neg | — |
| 16 | | 5715.5 | 2225.0 | neg | — | neg | — |
| 17 | | 5995.5 | 2334.0 | neg | — | neg | — |
| Positive control (low) | 156 ng/mL 1 | 1804.0 | 622.0 | pos | 30.5 | pos | 28.2 |
| | 2 | 1847.2 | 639.7 | pos | 31.3 | pos | 29.0 |
| Positive control (high) | 5000 ng/mL 1 | 5770.3 | 2177.9 | pos | 97.6 | pos | 98.8 |
| | 2 | 5755.5 | 2177.3 | pos | 97.4 | pos | 98.8 |

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention an and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

What is claimed is:

1. A method of detecting neutralizing antibodies to leptin in a test sample obtained from a human subject, wherein the test sample is a blood, serum, or plasma sample, the method comprising the steps of:
   (a) inactivating leptin present in the test sample;
   (b) adding a known quantity of labeled leptin to the test sample;
   (c) contacting the sample containing labeled leptin of (b) with a substrate capable of binding the labeled leptin;
   (d) washing the substrate to remove unbound labeled leptin;
   (e) measuring the label signal produced by the substrate-bound labeled leptin;
   (f) measuring a negative control signal, said negative control signal produced by completing steps (a)-(e) in a control blood, serum, or plasma sample that does not contain antileptin neutralizing antibodies; and
   (g) comparing the signal from (e) with the signal from (f), wherein if the level of signal measured in (e) is greater than or equal to the level of signal measured in (f), then the sample does not contain neutralizing antibodies to leptin, and wherein if the level of signal measured in (e) is less than the level of signal measured in (f), then the sample contains neutralizing antibodies to leptin.

2. A method of identifying human subjects having neutralizing antibodies to leptin in blood, serum, or plasma from the subject comprising the steps of:
   (a) inactivating leptin present in the sample of blood, serum, or plasma;
   (b) adding a known quantity of labeled leptin to the sample;
   (c) contacting the sample containing labeled leptin of (b) with a substrate capable of binding the labeled leptin;
   (d) washing the substrate to remove unbound labeled leptin;
   (e) measuring the label signal produced by the bound labeled leptin;
   (f) measuring a negative control signal, said negative control signal produced by completing steps (a)-(e), wherein the sample of blood, serum, or plasma does not contain antileptin neutralizing antibodies; and
   (g) comparing percent difference in the signal from (e) and the signal from (f) with a cutpoint, wherein if the percent difference in the signal from (e) and the signal from (f) is greater than the cutpoint, then the subject tests positive for anti-leptin neutralizing antibodies.

3. The method of claim 2, wherein the cutpoint is between about 5% and about 40%.

4. The method of claim 3, wherein the subject is a healthy subject, and the cutpoint is between about 7% and about 8%.

5. The method of claim 1, wherein the leptin is labeled with horseradish peroxidase, or ruthenium tris-bipyridine.

6. The method of claim 1, wherein the inactivation step (a) is accomplished by heating the sample.

7. The method of claim 1, wherein said substrate capable of binding the labeled leptin comprises:
   i. a coated matrix;
   ii. a tagged leptin receptor bound to the matrix of (i).

8. The method of claim 7, wherein the leptin receptor is tagged with biotin.

9. The method of claim 1, wherein said substrate capable of binding the labeled leptin comprises:
   i. a coated matrix;
   ii. an antibody bound to the matrix of (i); and
   iii. a tagged leptin receptor bound to the antibody of (ii).

10. The method of claim 9, wherein the leptin receptor is tagged with a tag suitable for affinity purification.

11. The method of claim 9, wherein the antibody has suitable affinity for the leptin receptor tag.

12. The method of claim 9, where the antibody is labeled with a tag suitable to bind to the coated matrix.

13. The method of claim 2, wherein the inactivation step (a) is accomplished by heating the sample.

14. The method of claim 2, wherein said substrate capable of binding the labeled leptin comprises:
   i. a coated matrix;
   ii. a tagged leptin receptor bound to the matrix of (i).

15. The method of claim 14, wherein the leptin receptor is tagged with biotin.

16. The method of claim 2, wherein said substrate capable of binding the labeled leptin comprises:
   i. a coated matrix;
   ii. an antibody bound to the matrix of (i); and
   iii. a tagged leptin receptor bound to the antibody of (ii).

17. The method of claim 16, wherein the leptin receptor is tagged with a tag suitable for affinity purification.

18. The method of claim 16, wherein the antibody has suitable affinity for the leptin receptor tag.

19. The method of claim 16, where the antibody is labeled with a tag suitable to bind to the coated matrix.

* * * * *